(12) United States Patent
Peters et al.

(10) Patent No.: US 8,143,067 B2
(45) Date of Patent: Mar. 27, 2012

(54) HYDROPHILIC, HIGH PROTEIN BINDING, LOW FLUORESCENCE, WESTERN BLOTTING MEMBRANE

(75) Inventors: Antoni Peters, Billerica, MA (US); Philip Goddard, Billerica, MA (US); John Charkoudian, Billerica, MA (US); Neil Soice, Billerica, MA (US); Dave Brewster, Billerica, MA (US); Anja Dedeo, Billerica, MA (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 12/938,813

(22) Filed: Nov. 3, 2010

(65) Prior Publication Data

US 2011/0045493 A1    Feb. 24, 2011

Related U.S. Application Data

(63) Continuation of application No. 12/462,635, filed on Aug. 6, 2009.

(60) Provisional application No. 61/189,302, filed on Aug. 18, 2008.

(51) Int. Cl.
C12Q 1/00 (2006.01)
G01N 33/53 (2006.01)
C12P 19/26 (2006.01)
B01D 57/02 (2006.01)

(52) U.S. Cl. ............. 436/86; 435/4; 435/6; 435/7.1; 435/401; 204/450; 436/71; 436/173

(58) Field of Classification Search ............. 210/645, 210/500.27, 500.35; 436/69.7, 71, 173, 91.2, 436/69, 86; 204/450, 456; 435/4–6, 7.1, 435/401
See application file for complete search history.

(56) References Cited

U.S. PATENT DOCUMENTS

| | | | |
|---|---|---|---|
| 4,618,533 A | 10/1986 | Steuck | |
| 4,678,813 A | 7/1987 | Itoh et al. | |
| 4,695,592 A | 9/1987 | Itoh et al. | |
| 4,906,374 A | 3/1990 | Gsell | |
| 4,944,879 A | 7/1990 | Steuck | |
| 4,968,533 A | 11/1990 | Gsell | |
| 5,019,260 A | 5/1991 | Gsell et al. | |
| 5,112,736 A | 5/1992 | Caldwell et al. | |
| 5,322,769 A * | 6/1994 | Bolling et al. | 435/5 |
| 5,470,710 A | 11/1995 | Weiss et al. | |
| 5,929,214 A | 7/1999 | Peters et al. | |
| 6,120,996 A * | 9/2000 | Belyavsky et al. | 435/6 |
| 6,153,596 A * | 11/2000 | Liotta et al. | 514/44 A |
| 6,558,734 B2 | 5/2003 | Koulik et al. | |
| 6,586,038 B1 | 7/2003 | Chabrecek et al. | |
| 6,710,098 B1 | 3/2004 | Lee et al. | |
| 7,073,671 B2 | 7/2006 | Charkoudian | |
| 7,284,668 B2 | 10/2007 | Charkoudian | |
| 7,419,778 B2 * | 9/2008 | Van Damme et al. | 435/4 |
| 7,482,668 B2 | 1/2009 | Hsieh et al. | |
| 7,648,034 B2 | 1/2010 | Charkoudian et al. | |
| 7,815,922 B2 | 10/2010 | Chaney et al. | |
| 2002/0012910 A1 | 1/2002 | Weiss et al. | |
| 2002/0150671 A1 | 10/2002 | Koulik et al. | |
| 2003/0077435 A1 | 4/2003 | Charkoudian et al. | |
| 2003/0226799 A1 | 12/2003 | Charkoudian | |
| 2004/0007459 A1 | 1/2004 | Herchen | |
| 2005/0133441 A1 | 6/2005 | Charkoudian | |
| 2006/0076288 A1 | 4/2006 | Mezhirov et al. | |

FOREIGN PATENT DOCUMENTS

| | | |
|---|---|---|
| EP | 0 138 144 A2 | 4/1985 |
| EP | 1 779 922 A1 | 5/2007 |
| WO | 95/11961 A1 | 5/1995 |
| WO | 98/01208 A1 | 1/1998 |
| WO | 02/087734 A1 | 11/2002 |
| WO | 03/103814 A1 | 12/2003 |
| WO | 2006/044463 A1 | 4/2006 |
| WO | 2008/040994 A2 | 4/2008 |

OTHER PUBLICATIONS

European Search Report dated Nov. 5, 2009 in corresponding foreign application (EP09168000).
Journal of Membrane Science, 55 (1991) 119-130; Hiroo Iwata et al.; "Preparation of temperature-sensitive membranes by graft polymerization onto a porous membane".
J. Am. Chem. Soc. 2000, 122, 8303-8304; Robert G. Chapman et al.; "Surveying for Surfaces that Resist the Adsorption of Proteins".
Journal of Membrane Science, 311 (2008) 294-305; Abdul Halim Mohd Yusof et al.; "Polypropylene-based membrane adsorbers via photo-initiated graft copolymerization: Optimizing separation performance by preparation conditions".
Office Action dated Feb. 8, 2011 in corresponding U.S. Appl. No. 12/462,635.

* cited by examiner

*Primary Examiner* — Ana Fortuna (74) *Attorney, Agent, or Firm* — Nields, Lemack & Frame, LLC (57) ABSTRACT

Hydrophilic membrane particularly suited for blotting applications, preferably Western blotting. A pre-wet hydrophobic membrane substrate, preferably made of PVDF, is contacted with a monomer solution and subjected to a UV-initiated free radical polymerization step to render the substrate permanently hydrophilic. The resulting membrane exhibits low background fluorescence, high protein binding, excellent retention of protein sample spot morphology, and extended dynamic range (high signal-to-noise ratio, enhanced sample detectability). The membrane demonstrates comparable or higher performance in Western blotting applications than conventional nitrocellulose Western blotting membranes, particularly for protein detection at low sample concentrations, and is directly water-wettable, eliminating the need for an alcohol pre-wet step prior to use.

8 Claims, 3 Drawing Sheets

HYDROPHILIC, HIGH PROTEIN BINDING, LOW FLUORESCENCE, WESTERN BLOTTING MEMBRANE

This application is a continuation of Ser. No. 12/462,635 filed Aug. 6, 2009, which claims priority of Provisional Application Ser. No. 61/189,302 filed Aug. 18, 2008, the disclosures of which are hereby incorporated by reference.

BACKGROUND OF THE INVENTION

"Blotting" or "electro-blotting" refers to the process used to transfer biological samples from a gel to a membrane under the influence of an electric field. The process requires a membrane that can immobilize biomolecular samples for subsequent detection. This places specific requirements on the membranes related to surface area, porosity, and protein binding capacity.

Western blotting is one modification of this technique that involves the immobilization of proteins on membranes before detection using monoclonal or polyclonal antibodies. Prior to protein immobilization on the membrane, sample proteins are separated using SDS polyacrylamide gel electrophoresis (SDS-PAGE) to separate native or denatured proteins. The proteins are then transferred or electro-blotted onto a membrane, where they are probed and ultimately detected using antibodies specific to a target protein. Western blotting membranes are typically made of nitrocellulose (NC) or polyvinylidene fluoride (PVDF). The specificity of the antibody-antigen interaction can enable a single protein to be identified among a complex protein mixture.

To summarize, Western blotting involves application of a protein sample (lysate) onto a polyacrylamide gel, subsequent separation of said complex mixture by electrophoresis, and transferal or "electro-blotting" of separated proteins onto a second matrix, generally a nitrocellulose or polyvinylidene fluoride (PVDF) membrane. Following the transfer, the membrane is "blocked" to prevent nonspecific binding of antibodies to the membrane surface. Many antibody labeling or tagging strategies are known to those skilled in the art. In the simplest protocols, the transferred proteins are incubated or complexed with a primary enzyme-labeled antibody that serves as a probe. After blocking non-specific binding sites a suitable substrate is added to complex with the enzyme, and together they react to form chromogenic, chemiluminescent, or fluorogenic detectable products that allow for visual, chemiluminescence, or fluorescence detection, respectively. The most sensitive detection schemes make use of chemiluminescent or fluorescent phenomena. In chemiluminescent detection, an enzyme-substrate complex produces detectable optical emissions (chemiluminescence). These emissions are recorded and measured using suitable detectors such as film or photonic devices. Absence or presence of signal indicates whether a specific protein is present in the lysate, and signal intensity is related to the level of the protein of interest, which in some cases may be quantifiable.

The use of nitrocellulose membranes is ubiquitous in immunodetection assay work, particularly in Western blotting. This is partially due to historical considerations, and partially due to ease of use. Nitrocellulose blotting membranes do not require an organic liquid pre-wet step, a requirement for working with hydrophobic membranes. Hydrophobic membranes require an alcohol pre-wet step followed by a water exchange step (for alcohol removal), before assembly within the blot-transfer assembly. Intrinsically hydrophobic membranes afford a limited time-frame for this assembly; the potential for the membrane to dry out is significant. Once dry, the membrane cannot be re-wet unless the pre-wet sequence is repeated. Once the membrane is contacted to the gel, removal prior to transfer can effectively ruin the gel and the separated protein samples contained. The pre-wet step is time consuming and can considerably impede workflow. A hydrophilic membrane will remain wet for a longer time interval, and can be re-wet with water if it does dry out before assembly.

Nitrocellulose blotting membranes are water wet-able and show satisfactory performance for most blotting applications. But nitrocellulose is not as mechanically or chemically stable as PVDF. PVDF will maintain its mechanical integrity over a long timeframe, whereas NC will become brittle and discolored. PVDF membrane blots can be stripped of antibodies and be re-probed. NC blots cannot. NC is prone to air oxidation, wherein it can become hazardous. It requires a separate waste stream, and when disposed of must be damped with a wetting agent, usually water.

Hydrophobic PVDF blotting membranes possess equivalent protein binding ability to NC blotting membranes, but exhibit superior blotting performance. Much lower sample concentrations can be detected under the same conditions on these PVDF membranes compared to NC. Low-background fluorescence hydrophobic PVDF blotting membranes exhibit the same enhanced sample detection while enabling the use of fluorescent detection schemes.

It therefore would be desirable to provide a hydrophilic PVDF membrane for immunodetection assays such as Western blotting, with performance characteristics that approach the lower sample detection limits and low background fluorescence that are characteristic of hydrophobic PVDF membranes. This invention addresses these requirements.

SUMMARY OF THE INVENTION

Those skilled in the art of surface modification for the purpose of altering substrate surface energies, and in particular with regard to surfaces intended for contact with biological systems, will concur that hydrophilic surface modifications traditionally exhibit low protein binding behavior. The embodiments disclosed herein build on the serendipitous and unexpected discovery that space polymers derived from certain monomeric acrylamide mixtures, and formed using free-radical polymerization reactions, can give rise to surface modifications that are not only hydrophilic, but also demonstrate a high level of protein binding.

Much of the prior art describes the use of hydroxyl containing monomers, usually carbonyl ester containing acrylate polymers, to produce membrane surface modifications having hydrophilic character and high resistance to protein binding. However, it is known that polymers from such monomers are not resistant to strong alkaline solutions. For example, a solution of 1.0 normal sodium hydroxide will hydrolyze the carbonyl containing acrylate polymers to acrylic acid containing polymers. Such acrylic acid containing polymers are ionically charged under certain pH conditions, and will attract and bind oppositely charged proteins or biomolecules, thus increasing sorption and membrane fouling. In addition, acrylic acid containing polymers swell in water to an extent that they constrict pore passages, thus reducing membrane permeability and productivity. Moreover, polymers from hydroxyl containing monomers, such as hydroxy acrylates, further react in strong alkaline solutions and degrade into soluble low molecular weight fragments, which dissolve away and expose the underlying substrate porous media or membrane.

Practitioners attempting to develop optimized membranes either for filtration or non-filtration applications in the pharmaceutical and biotechnology industries must overcome significant problems. Facing stringent cost, performance and safety requirements, a practitioner must use materials and develop manufacturing methods that produce membranes with not only optimized flow and retention characteristics, but be economical to produce, meet cleanliness criteria, be stable to the various chemical environments which are commonly encountered, and be very either very resistant to biomolecule adsorption, or very strongly adsorbing, depending upon the intended end-use. Thus, in this instance, it is very desirable to have a membrane modification that results in a hydrophilic, biomolecule adsorptive surface that is heat stable, which is resistant to degradation by any potential reagent solutions, and which has very low levels of material capable of being extracted there-from.

Protein binding results from early investigations into mixed-acrylamide polymeric surface modifications indicated that certain mixtures of hydrophilic bis-acrylamide crosslinking monomers and monofunctional neutral or charged acrylamides can, when copolymerized using UV-initiated or electron beam-initiated free-radical techniques, produce high protein-binding hydrophilic surface modifications. However, initial starting levels of each monomer had to be severely decreased before observing satisfactory dot blot morphology and blotting transfer performance.

The problems of the prior art have been overcome by the present embodiments, which provide a hydrophilic membrane particularly suited for blotting applications, preferably Western blotting. More specifically, a pre-wet hydrophobic membrane substrate, preferably made of PVDF, is contacted with a monomer solution and subjected to polymerizing conditions to render the substrate permanently hydrophilic.

The resulting membrane exhibits low background fluorescence, high protein binding, excellent retention of protein sample spot morphology, and extended dynamic range (high signal-to-noise ratio, enhanced sample detectability). Where chemiluminescence is used for detection, the level of background fluorescence inherent in the unmodified parent membrane is not as critical. The membrane demonstrates comparable or higher performance in Western blotting applications than conventional nitrocellulose blotting membranes, particularly for detection at low sample concentrations, and is directly water-wettable, eliminating the need for an alcohol pre-wet step prior to use. The membrane exhibits complete, instant, and uniform wetting upon contact with water, and exhibits delayed wetting when contacted with a saturated aqueous aluminum chloride solution. That is, when said membrane is placed on the surface of this saturated aqueous aluminum chloride solution, it wets through in a minimum time interval of not less than 1 second).

DETAILED DESCRIPTION

The membranes hydrophilically modified in accordance with embodiments of the present disclosure provide immunodetection assay platforms that are comparable to, or exhibit superior blotting performance to nitrocellulose membranes, particularly with respect to expansion of the low end of the dynamic range of sample detectability. For example, in FIG. 1, Western blotting results from a typical development run demonstrate the performance differences between the hydrophilic PVDF blotting membrane of this invention, and the controls (FL—hydrophobic PVDF membrane, and NC—Whatman/S&S BA-85 membrane). Each horizontal strip in the figure contains 5 separate Western transfer blots; three blots on hydrophilic PVDF development samples, and one blot on each of the control membranes. Each horizontal strip of 5 Western blots is the result from one electrophoresis and transfer experiment (5 gels followed by 5 blots were run in each experiment). By design, each experiment embodies identical conditions on each gel/blot with identical quantities of protein sample (applied in 4 lanes across each gel) before electrophoresis and transfer. The results shown are the recorded (chemiluminescent) transfer blots for the detection of 2 proteins (HSP70 and GAPDH) from a complex sample mixture (lysate), applied at decreasing sample concentrations, from left-to-right on each gel, and corresponding to: 5 ug, 2.5 ug, 1.25 ug, 0.67 ug.

Suitable porous membranes include those formed from aromatic sulfone polymers, polytetrafluoroethylene, perfluorinated thermoplastic polymers, polyolefin polymers, ultra-high molecular weight polyethylene, polyamides including Nylon 6 and Nylon 66, and polyvinylidene fluoride, with polyvinylidene fluoride being particularly preferred. Porous membranes include both microporous membranes and ultrafiltration membranes, and are preferably in the form of sheets. Generally the average pore sizes include those between 0.001 and 10 microns. Blotting membranes are nominally 0.45 um pore size materials. Preferred starting membranes have a porosity (void volume) range specification of 68-73%. Blotting membranes are traditionally symmetric. However, the coating could be applied to an asymmetric membrane.

The polymeric coating can be a copolymer or terpolymer formed from at least one polyfunctional monomer modified with at least one hydrophilic functional group, said hydrophilic polyfunctional monomer(s) selected from the group consisting of polyfunctional acrylamides, polyfunctional methacrylamides and diacroylpiperazines, and formed from at least one monofunctional monomer modified with at least one hydrophilic functional group, said hydrophilic monofunctional monomer(s) selected from the group consisting of monofunctional acrylamides, monofunctional methacrylamides, and acryloyl piperazines.

It was found that a porous hydrophobic membrane, preferably one made of polyvinylidene fluoride coated with a crosslinked acrylamide-ethylene-bis-acrylamide copolymer was rendered highly hydrophilic. Furthermore, at the copolymer level that was applied to the porous PVDF membrane samples in early iterations of this invention, IgG binding assays revealed protein binding levels to be in the neighborhood of 400 ug/cm$^2$. This level is typical of the parent hydrophobic PVDF membrane and of conventional nitrocellulose membranes. The first surprising result was that membranes so prepared were both hydrophilic, and high protein-binding. However, the Western blotting performance of these initial samples (those that exhibited this high level of protein binding) was not satisfactory in terms of maintaining small sample blot size (blot morphology), and in terms of sample capture in blot transfers. By modifying the copolymer coating level, satisfactory blotting performance was realized. At these modified levels, protein binding levels were reduced to between 250 and 325(00) ug/cm$^2$, but Western blotting performance rose to levels intermediate between nitrocellulose and the preferred parent hydrophobic PVDF membrane. Surprisingly, the present inventors found that the protein binding level is not the best or only predictor of Western blotting membrane performance. Sacrificing some protein binding ability by modifying the coating level on the substrate can result in improved blotting performance.

Thus, component levels and relative concentrations of the modifying formulation are critical to obtain acceptable immunodetection assay performance. A low overall solids concentration in a highly specific component ratio balances water-wetting performance against blotting performance. The very low background fluorescence level of the substrate membrane is preserved. If, however, the level of surface modification chemistry is too low, the result is a membrane that is not water-wettable to an acceptable extent. If the level of surface modification is too high the resulting membranes exhibit extremely high surface energies. As stated earlier, at higher levels of surface modifying chemistry, the measured protein binding capacity is roughly equivalent to nitrocellulose and hydrophobic PVDF membranes, but poor electroblotting performance results.

In accordance with certain embodiments, the total solids level in the modifying/reactant solution is to be adjusted to between 0.90% and 1.10% by weight. A total solids concentration in this range with the specified component ratio results in optimal blotting performance. This formulation includes a UV-photoinitiator component.

Suitable amounts of the acrylamide monofunctional monomer and the bis-acrylamide crosslinking monomer in the reactant solution are to be between 0.20% and 2.00% by weight (each), preferably with amounts between 0.30% and 0.60% by weight (each), and most preferably between 0.40% and 0.50% by weight (inclusive, each). The preferred ratio of acrylamide to bis-acrylamide of the monomer reactant solution is about 1:1 (mass/mass). The preferred overall monomer concentration of acrylamide:methylene-bis-acrylamide monomer reactant solution is between 0.5% and 1.5% by mass. A suitable UV-photoinitiator component is present in 0.01% to 0.20% by weight preferably between 0.05 and 0.15% by weight, and most preferably between 0.09% and 0.11%, by weight. Suitable UV-photoinitiators include Irgacure 500, 754, 2959, and 819DW. Methods for preparation of the modified porous membrane substrate in accordance with certain embodiments include the steps of providing a porous membrane substrate, contacting the surface of the porous membrane substrate with a reactant solution comprising acrylamide and methylene-bis-acrylamide, and a suitable photoinitiator, removing the membrane from the solution, and polymerizing the coating in situ on the membrane substrate by exposing the same to radiation of a suitable wavelength and intensity for a suitable time interval. Preferably the porous membrane contacted with the reaction solution is irradiated with an ultraviolet light source. Filters may be used to reduce or eliminate undesirable wavelengths which may cause damage to the porous membrane. The amount of exposure time to the UV light and the intensity thereof should be familiar to those skilled in the art.

In the preferred embodiment of the invention, a laboratory-scale preparation of the reactant monomer solution is made by dissolving 1.00 g acrylamide, [$H_2C$=CH—C(O)—$NH_2$] monofunctional monomer; 0.80 g methylene-bis-acrylamide, [$H_2C$(—NH—C(O)CH=$CH_2$)$_2$] cross-linking monomer; and, 0.20 g Irgacure 2959 photo-initiator into 198.00 g of Milli-Q® water. An extended mixing interval of about 2 hours is required to fully dissolve the cross-linker and the photo-initiator.

More specifically, the porous hydrophobic starting membrane is pre-wet by immersion in an organic liquid or in an aqueous solution thereof that does not swell or dissolve the porous membrane, and which pre-wets the entire porous surface of the membrane.

The liquid may be a low molecular weight alcohol, or a mixture of water and a miscible organic liquid. Suitable liquids or compositions include methanol, ethanol, isopropanol, water mixtures thereof, acetone/water mixtures, and tetrahydrofuran/water mixtures of sufficiently low surface tension to affect wetting the entire membrane surface.

The purpose of this pre-wetting step is to assure that the entire membrane surface is rendered wettable by water, and subsequently by the aqueous reactant monomer solution. The pre-wetting step must be followed by a rigorous exchange step with water to eliminate the presence of the organic solvent. These pre-wetting solvents or water mixtures thereof can exert a negative influence upon the intended polymerization of the reactant monomers.

Subsequent immersion and gentle agitation of the water-wet porous membrane in the reactant solution allows the entire surface of the porous membrane to be wet with reactant solution. As long as excess water is removed from the membrane prior to immersion in the reactant solution, no significant dilution of the reactant solution will occur.

The sample is withdrawn after a short (two minute) time interval and excess reactant solution is removed from the membrane sample. The reactant solution-wetted membrane is anaerobically exposed to UV radiation to effect the polymerization directly onto the entire porous membrane surface. The resulting coated membrane exhibits: Immediate, complete, and thoroughly uniform wetting when contacted onto a water surface; A high level of Western blotting performance; A high level of protein binding ($\geqq 250$ ug/cm$^2$ IgG) by radio-labeled assay; and, Low background fluorescence (about 2000 rfu @485 nm/535 nm excitation/emission wavelengths using a TECAN GENios FL fluorescence reader with detector gain set at 86, and running Magellan 5.0 software package), which is about twice the background fluorescence of the untreated (unmodified parent hydrophobic) membrane under the same measurement conditions. When placed on the surface of a saturated aqueous aluminum chloride solution, the membrane will wet through in a minimum time interval of not less than 1 second, and in a maximum time interval that may exceed 60 seconds.

EXAMPLE 1

Commercially available hydrophobic PVDF membrane from Millipore Corporation (IPFL00000) was immersed in methyl alcohol. The membrane was withdrawn and immersed in water with agitation to extract methanol for 1 minute. The membrane was withdrawn and immersed in fresh water for an additional 2-minute interval and then placed in fresh water before immersion in reactant monomer solution. Excess water was drained from the membrane and the membrane was then immersed in monomer reactant solution with gentle agitation for 2 minutes. Membrane was then exposed to UV radiation from both sides in a UV curing process at a line speed of 15 to 25 fpm. Membrane was recovered and placed into a water bath to remove unreacted monomer and non-adhering oligomers and polymer. Samples were dried either in air at room temperature overnight, or in a static forced-air oven between 60° C. and 80° C. for 10 minutes, or on an impingement dryer at 90-110° C. at a line speed of 15 to 25 fpm. Average membrane extractables as determined by an in-house TOC (Total Organic Carbon) method were measured to be about 1.44 ug/cm2, as shown in Table 1.

TABLE 1

Total Organic Carbon (TOC)—Five (5) 47 mm disks.

| Requestor ID: MIL6UJP37 | PVDF Hydrophillic IPFL Membrane Received |
| --- | --- |
| Requestor: Antoni Peters | For Blotting and Immuno Assays Applications |
| | Ext. for TOC Analysis |
| | Extraction By: A. Pervez |
| | TOC By: M. Santos-Rosa & A. Pervez |
| | Date: Oct. 16-19, 2006 |

| Ext. Solvent | Ext. Temp. [° C.] | Ext. Time [Hours] | Ext. Vol. [g] | Ext. Area [cm2] |
| --- | --- | --- | --- | --- |
| MilliQ Water | Ambient | 24 | 40 | 86.75 |

Summary Results

| Sample ID | TOC Acid/Oxid [µL/min] | TOC [ppm C] | Corrected TOC [ppm C] | TOC [µg C] | TOC [µg C/cm2] |
| --- | --- | --- | --- | --- | --- |
| Water Blank | 0.20/0.20 | 0.0639 | | | |
| T102 072806 A:-MBAM/AC/I-2959 | 0.75/1.00 | 3.29 | 3.23 | 129 | 1.49 |
| T102 072806 B:-MBAM/AC/I-2959 | 0.75/1.00 | 2.91 | 2.85 | 114 | 1.31 |
| T102 072806 C:-MBAM/AC/I-2959 | 0.75/1.00 | 3.33 | 3.27 | 131 | 1.51 |

Average extractable residual monomer levels were determined by HPLC. Values determined from 3 samples are provided in Table 2.

TABLE 2

Extractable Monomer Levels by HPLC—Same samples as shown in Table 1.

| Sample | Acrylamide (µg/cm2) | MBAM (µg/cm2) | Irgacure 2959 (µg/cm2) |
| --- | --- | --- | --- |
| T102 072806A | 0.002 | 0.105 | N.D. |
| T102 072806B | 0.005 | 0.091 | N.D. |
| T102 072806C | 0.011 | 0.094 | N.D. |

EXAMPLE 2

The procedure of Example 1 was used to treat PVDF membranes having the specifications, treatment conditions and reactant solutions shown in Tables 3A-D, 4A-D, and 5A-D.

TABLE 3A

MODIFICATION DATA for Hydrophilic PVDF Western Blotting Membrane

| Roll No. | Monomer Mix Lot# | Starting Membrane Lot Data | Membrane Casting Dryer Temperature (F.) | Starting Membrane Properties | | | |
| --- | --- | --- | --- | --- | --- | --- | --- |
| | | | | Thick (um) | Porosity (%) | Bbl Pt (psi) | Flow Time (seconds) |
| RUN R—No Mix Ajustment—Footage VS Monomer Mix Concentration | | | | | | | |
| NA | NA | NA | NA | NA | NA | NA | NA |
| R01 | R Mix 1 | IPFL 071007 T214 | 300 | 112 | 72.8 | 9.4 | 56.0 |
| R02 | R Mix 1 | IPFL 071007 T205 | 300 | 113 | 73.0 | 9.4 | 63.0 |
| R03 | R Mix 1 | IPFL 071007 T205 | 300 | 113 | 73.0 | 9.4 | 63.0 |
| R04 | R Mix 1 | IPFL 071007 T205 | 300 | 113 | 73.0 | 9.4 | 63.0 |
| R05 | R Mix 1 | IPFL 071007 T205 | 300 | 113 | 73.0 | 9.4 | 63.0 |
| R06 | R Mix 1 | IPFL 071007 T206 | 300 | 111 | 72.4 | 9.5 | 65.0 |
| R07 | R Mix 1 | IPFL 071007 T206 | 300 | 111 | 72.4 | 9.5 | 65.0 |
| R08 | R Mix 1 | IPFL 071007 T206 | 300 | 111 | 72.4 | 9.5 | 65.0 |
| R09 | R Mix 1 | IPFL 071007 T206 | 300 | 111 | 72.4 | 9.5 | 65.0 |
| R10 | R Mix 1 | IPFL 071007 T214 | 300 | 112 | 72.8 | 9.4 | 56.0 |
| R11 | R Mix 1 | IPFL 071007 T214 | 300 | 112 | 72.8 | 9.4 | 56.0 |
| R12 | R Mix 1 | IPFL 071007 T214 | 300 | 112 | 72.8 | 9.4 | 56.0 |
| R12 End | NA | NA | 300 | NA | NA | NA | NA |

TABLE 3B

MODIFICATION DATA for Hydrophilic PVDF Western Blotting Membrane

| | | Monomer Mix Component Concentrations | | | | |
|---|---|---|---|---|---|---|
| Roll No. | Monomer Mix Sample ID | Actual AC Wt % (HPLC) | Actual MBAM Wt % (HPLC) | Actual I-2959 Wt % (HPLC) | Actual Total Solids Wt % (HPLC) | Totalized Footage By Roll |
| RUN R—No Mix Ajustment—Footage VS Monomer Mix Concentration | | | | | | |
| NA | R Mix 1 DRUM | 0.5156 | 0.4214 | 0.1130 | 1.0500 | 0 |
| R01 | MM1 Start | 0.5091 | 0.4042 | 0.1102 | 1.0235 | 0 |
| R02 | MM2 | 0.5105 | 0.3957 | 0.1094 | 1.0156 | 500 |
| R03 | MM3 | 0.5038 | 0.3837 | 0.1055 | 0.9931 | 800 |
| R04 | MM4 | 0.4996 | 0.3773 | 0.1001 | 0.9771 | 1100 |
| R05 | MM5 | 0.4948 | 0.3708 | 0.0999 | 0.9655 | 1250 |
| R06 | MM6 | 0.4935 | 0.3685 | 0.1020 | 0.9640 | 1550 |
| R07 | MM7 | 0.4868 | 0.3618 | 0.0995 | 0.9481 | 1850 |
| R08 | MM8 | 0.4868 | 0.3605 | 0.0974 | 0.9448 | 2150 |
| R09 | MM9 | 0.4777 | 0.3553 | 0.0956 | 0.9286 | 2300 |
| R10 | MM10 | 0.4721 | 0.3528 | 0.0956 | 0.9204 | 2600 |
| R11 | MM11 | 0.4673 | 0.3521 | 0.0932 | 0.9125 | 2900 |
| R12 | MM12 | 0.4682 | 0.3561 | 0.0918 | 0.9161 | 3200 |
| R12 End | MM13 End | 0.4574 | 0.3546 | 0.0879 | 0.8999 | 3300 |

TABLE 3C

MODIFICATION DATA for Hydrophilic PVDF Western Blotting Membrane

| Roll No. | Nip Aisle Press psi | Nip Wall Press psi | Line Speed ft/min | Lamps Type/No | Lamps Config | UV Chamber Conditions | | | | |
|---|---|---|---|---|---|---|---|---|---|---|
| | | | | | | $N_2$ Flow Top/Bottom (SCFM) | UV P1 Inch HWC | UV P3 Inch HWC | UV P2 Inch HWC | Starting $O_2$ Level (ppm) |
| RUN R—No Mix Ajustment—Footage VS Monomer Mix Concentration | | | | | | | | | | |
| NA | NA | NA | NA | NA | NA | NA | 1.0 | 1.6 | 1.0 | 90.0 |
| R01 | 20 | 20 | 20 | H/4 | Staggered | 10/9.5 | 1.1 | 1.7 | 1.1 | 70.0 |
| R02 | 20 | 20 | 20 | H/4 | Staggered | 10/9.5 | 1.1 | 1.7 | 1.1 | 56.7 |
| R03 | 20 | 20 | 20 | H/4 | Staggered | 10/9.5 | 1.1 | 1.7 | 1.1 | 39.3 |
| R04 | 20 | 20 | 20 | H/4 | Staggered | 10/9.5 | 1.1 | 1.7 | 1.1 | 33.0 |
| R05 | 20 | 20 | 20 | H/4 | Staggered | 10/9.5 | 1.1 | 1.7 | 1.1 | 28.8 |
| R06 | 20 | 20 | 20 | H/4 | Staggered | 10/9.5 | 1.1 | 1.7 | 1.1 | 27.8 |
| R07 | 20 | 20 | 20 | H/4 | Staggered | 10/9.5 | 1.1 | 1.7 | 1.1 | 26.9 |
| R08 | 20 | 20 | 20 | H/4 | Staggered | 10/9.5 | 1.1 | 1.7 | 1.1 | 26.4 |
| R09 | 20 | 20 | 20 | H/4 | Staggered | 10/9.5 | 1.1 | 1.7 | 1.1 | 27.4 |
| R10 | 20 | 20 | 20 | H/4 | Staggered | 10/9.5 | 1.1 | 1.7 | 1.1 | 25.2 |
| R11 | 20 | 20 | 20 | H/4 | Staggered | 10/9.5 | 1.1 | 1.7 | 1.1 | 27.1 |
| R12 | 20 | 20 | 20 | H/4 | Staggered | 10/9.5 | 1.1 | 1.7 | 1.1 | 27.8 |
| R12 End | NA | NA | NA | NA | NA | NA | 1.1 | 1.7 | 1.1 | 25.2 |

TABLE 3D

MODIFICATION DATA for Hydrophilic PVDF Western Blotting Membrane

| Roll No. | Water Wet Speed OK? | Water Wet Uniform X-web? | Water Wet Through OK? | Salt Wet Time Seconds | Salt Wet Time Seconds | Salt Wet Time Seconds | Salt Wet Time Seconds | Fluores BKG RFU | QC Blotting Pass/Fail Control | Western Blotting Live Lysate |
|---|---|---|---|---|---|---|---|---|---|---|
| RUN R—No Mix Ajustment—Footage VS Monomer Mix Concentration | | | | | | | | | | |
| NA | NA | NA | NA | NA | NA | NA | NA | NA | NA | ≧NC |
| R01 | Y | Y | Y | 4.7 | 3.5 | 3.0 | 3.7 | 1750.57 | Pass 9 Band | ≧NC |
| R02 | Y | Y | Y | 1.4 | 2.4 | 2.4 | 2.1 | N/Avail. | N/Avail. | ≧NC |
| R03 | Y | Y | Y | 1.4 | 2.4 | 2.4 | 2.1 | N/Avail. | N/Avail. | ≧NC |
| R04 | Y | Y | Y | 2.1 | 2.2 | 2.5 | 2.3 | N/Avail. | N/Avail. | ≧NC |
| R05 | Y | Y | Y | 2.9 | 3.1 | 2.9 | 3.0 | 2015.63 | Pass 9 Band | ≧NC |
| R06 | Y | Y | Y | 2.2 | 2.3 | 2.3 | 2.3 | N/Avail. | N/Avail. | ≧NC |
| R07 | Y | Y | Y | 4.1 | 3.9 | 4.0 | 4.0 | N/Avail. | N/Avail. | ≧NC |
| R08 | Y | Y | Y | 2.3 | 3.7 | 3.2 | 3.1 | N/Avail. | N/Avail. | ≧NC |
| R09 | Y | Y | Y | 5.7 | 7.3 | 5.3 | 6.1 | 1927.95 | Pass 9 Band | ≧NC |

TABLE 3D-continued

MODIFICATION DATA for Hydrophilic PVDF Western Blotting Membrane

| Roll No. | Water Wet Speed OK? | Water Wet Uniform X-web? | Water Wet Through OK? | Salt Wet Time Seconds | Salt Wet Time Seconds | Salt Wet Time Seconds | Salt Wet Time Seconds | Fluores BKG RFU | QC Blotting Pass/Fail Control | Western Blotting Live Lysate |
|---|---|---|---|---|---|---|---|---|---|---|
| R10 | Y | Y | Y | 5.4 | 7.1 | 5.4 | 6.0 | N/Avail. | N/Avail. | ≧NC |
| R11 | Y | Y | Y | 6.3 | 7.5 | 5.6 | 6.5 | N/Avail. | N/Avail. | ≧NC |
| R12 | Y | Y | Y | 8.5 | 7.8 | 7.6 | 8.0 | 1708.5 | Pass 9 Band | ≧NC |
| R12 End | Y | Y | Y | 16.7 | 16.5 | 16.3 | 16.5 | NA | NA | ≧NC |

TABLE 4A

MEMBRANE MODIFICATION DATA—Hydrophilic PVDF Western Blotting Membrane

| Run Segment | Roll No. | Monomer Mix Lot# | Starting Membrane Lot Data | Heat Treat Temperature or Mod Line Dryer Temperature | Membrane Casting Dryer Temperature |
|---|---|---|---|---|---|
| RUN S—POROSITY/THICKNESS, VMF4 DRYER TEMP, LINESPEED | | | | | |
| NA | NA | NA | NA | | |
| Test | R01 | S Mix 1 | IPFL 071007 T203 | 205 | 300 |
| S1 | R02 | S Mix 1 | IPX 070907 R103 | 205 | 300 |
| S1 | R03 | S Mix 1 | IPX 091407 T103 | 205 | 310 |
| S1 | R04 | S Mix 1 | IPX 120307 T107 | 205 | 300 |
| S1 | R05 | S Mix 1 | IPX 091407 T102 | 205 | 310 |
| S1 | R06 | S Mix 1 | IPX 070907 R105 | 204 | 300 |
| S2 | R07 | S Mix 1 | IPX 120307 T107 | 200 | 300 |
| S2 | R08 | S Mix 1 | IPX 120307 T107 | Transition | 300 |
| S2 | R09 | S Mix 1 | IPX 120307 T107 | 205 | 300 |
| S2 | R10 | S Mix 1 | IPX 120307 T107 | Transition | 300 |
| S2 | R11 | S Mix 1 | IPX 120307 T107 | 210 | 300 |
| S2 | R12 | S Mix 1 | IPX 120307 T107 | 210 | 300 |
| S2 | R13 | S Mix 1 | IPX 120307 T107 | 210 | 300 |

Segment 1 Variation of starting membrane properties
Segment 2 Variation of line speed and dryer temperature

TABLE 4B

MEMBRANE MODIFICATION DATA—Hydrophilic PVDF Western Blotting Membrane

| Run Segment | Roll No. | Thick (um) | Porosity (%) | Bbl Pt (psi) | Flow Time (seconds) | Monomer Mix Sample ID | Actual AC Wt % (HPLC) | Actual MBAM Wt % (HPLC) | Actual I-2959 Wt % (HPLC) | Actual Total Solids Wt % (HPLC) | Totalized Footage By Roll |
|---|---|---|---|---|---|---|---|---|---|---|---|
| RUN S—POROSITY/THICKNESS, VMAF4 DRYER TEMP, LINESPEED | | | | | | | | | | | |
| NA | NA | NA | NA | NA | NA | MM1B | 0.4979 | 0.3894 | 0.1005 | 0.9878 | 150 |
| Test | R01 | 112 | 72.8 | 9.6 | 61.0 | MM1C start | 0.4926 | 0.3877 | 0.1005 | 0.9808 | 300 |
| S1 | R02 | 115 | 74.8 | 9.3 | 55.0 | MM2B | 0.4893 | 0.3849 | 0.0996 | 0.9738 | 450 |
| S1 | R03 | 115 | 66.4 | 9.6 | 59.0 | MM3B | 0.4812 | 0.3785 | 0.0971 | 0.9568 | 600 |
| S1 | R04 | 126 | 72.9 | 9.4 | 65.0 | MM4B | 0.4780 | 0.3760 | 0.0963 | 0.9503 | 750 |
| S1 | R05 | 122 | 66.2 | 11.1 | 78.3 | MM5B | 0.4761 | 0.3733 | 0.0954 | 0.9448 | 950 |
| S1 | R06 | 130 | 74.7 | 10.7 | 74.0 | MM6B | 0.4785 | 0.3757 | 0.0953 | 0.9495 | 1100 |
| S2 | R07 | 126 | 72.9 | 9.4 | 65.0 | MM7B | 0.4699 | 0.3678 | 0.0934 | 0.9311 | 1200 |
| S2 | R08 | 126 | 72.9 | 9.4 | 65.0 | MM8B | 0.4673 | 0.3656 | 0.0926 | 0.9255 | 1305 |
| S2 | R09 | 126 | 72.9 | 9.4 | 65.0 | MM9B | 0.4660 | 0.3644 | 0.0925 | 0.9229 | 1405 |
| S2 | R10 | 126 | 72.9 | 9.4 | 65.0 | MM10B | 0.4655 | 0.3637 | 0.0917 | 0.9209 | 1505 |
| S2 | R11 | 126 | 72.9 | 9.4 | 65.0 | MM11B | 0.4642 | 0.3619 | 0.0910 | 0.9171 | 1605 |
| S2 | R12 | 126 | 72.9 | 9.4 | 65.0 | MM12B | 0.4618 | 0.3598 | 0.0903 | 0.9119 | 1705 |
| S2 | R13 | 126 | 72.9 | 9.4 | 65.0 | MM13B | Not Available | Not Available | Not Available | Not Available | 1855 |

Segment 1 Variation of starting membrane properties
Segment 2 Vaiation of line speed and dryer temperature

TABLE 4C

MEMBRANE MODIFICATION DATA—Hydrophilic PVDF Western Blotting Membrane

| Run Segment | Roll No. | Nip Aisle Press psi | Nip Wall Press psi | Line Speed ft/min | UV Chamber Conditions N₂ Flow Top/Bottom (SCFM) | UV P1 Inch HWC | UV P3 Inch HWC | UV P2 Inch HWC | Starting O₂ Level (ppm) |
|---|---|---|---|---|---|---|---|---|---|
| RUN S—POROSITY/THICKNESS, VMF4 DRYER TEMP, LINESPEED ||||||||||
| NA | NA | NA | NA | NA | NA | NA | NA | NA | NA |
| Test | R01 | 20 | 20 | 20 | 10/9.5 | 1.0 | 1.5 | 1.1 | 15.0 |
| S1 | R02 | 20 | 20 | 20 | 10/9.5 | 1.0 | 1.5 | 1.1 | 42.0 |
| S1 | R03 | 20 | 20 | 20 | 10/9.5 | 1.0 | 1.5 | 1.1 | 40.0 |
| S1 | R04 | 20 | 20 | 20 | 10/9.5 | 1.0 | 1.5 | 1.1 | 40.0 |
| S1 | R05 | 20 | 20 | 20 | 10/9.5 | 1.0 | 1.5 | 1.1 | 40.0 |
| S1 | R06 | 20 | 20 | 20 | 10/9.5 | 1.0 | 1.5 | 1.1 | 40.0 |
| S2 | R07 | 20 | 20 | 22 | 10/9.5 | 1.0 | 1.4 | 1.1 | 53.7 |
| S2 | R08 | 20 | 20 | 20 | 10/9.5 | 1.0 | 1.4 | 1.1 | 39.1 |
| S2 | R09 | 20 | 20 | 20 | 10/9.5 | 1.0 | 1.4 | 1.1 | 37.6 |
| S2 | R10 | 20 | 20 | 18 | 10/9.5 | 1.0 | 1.4 | 1.1 | 33.0 |
| S2 | R11 | 20 | 20 | 18 | 10/9.5 | 1.0 | 1.4 | 1.1 | 30.5 |
| S2 | R12 | 20 | 20 | 20 | 10/9.5 | 1.0 | 1.4 | 1.1 | 24.9 |
| S2 | R13 | 20 | 20 | 25 | 10/9.5 | 1.0 | 1.4 | 1.1 | 25.2 |

Segment 1 Variation of starting membrane properties
Segment 2 Vaiation of line speed and dryer temperature

TABLE 4D

MEMBRANE MODIFICATION DATA—Hydrophilic PVDF Western Blotting Membrane

| Run Segment | Roll No. | Water Wet Speed OK? | Water Wet Uniform X-web? | Water Wet Through OK? | Salt Wet Time Seconds | Salt Wet Time Seconds | Salt Wet Time Seconds | Salt Wet Time Seconds | Fluores BKG RFU | QC Blotting Pass/Fail Control | Western Blotting Live Lysate |
|---|---|---|---|---|---|---|---|---|---|---|---|
| RUN S—POROSITY/THICKNESS, VMF4 DRYER TEMP, LINESPEED ||||||||||||
| NA | NA | NA | NA | NA | NA | NA | NA | NA | NA | NA | NA |
| Test | R01 | Y | Y | Y | 8.2 | 8.8 | 4.9 | 7.3 | N/Avail. | N/Avail. | ≧NC |
| S1 | R02 | Y | Y | Y | 26.2 | 15.2 | 5.3 | 15.6 | N/Avail. | N/Avail. | ≧NC |
| S1 | R03 | Y | Y | Y | 4.2 | 4.2 | 2.9 | 3.8 | N/Avail. | N/Avail. | ≧NC |
| S1 | R04 | Y | Y | Y | 5.4 | 13.6 | 10.3 | 9.8 | N/Avail. | N/Avail. | ≧NC |
| S1 | R05 | Y | N | N | 7.8 | 4.6 | 5.7 | 6.0 | N/Avail. | N/Avail. | ≧NC |
| S1 | R06 | Y | Y | Y | 12.7 | 8.0 | 9.9 | 10.2 | N/Avail. | N/Avail. | ≧NC |
| S2 | R07 | Y | Y | Y | >120* | 90.0 | 25.0 | Meaningless | N/Avail. | N/Avail. | ≧NC |
| S2 | R08 | Y | Y | Y | >120* | >120 | 40.0 | Meaningless | N/Avail. | N/Avail. | ≧NC |
| S2 | R09 | Y | Y | Y | >120* | >120 | 30.0 | Meaningless | N/Avail. | N/Avail. | ≧NC |
| S2 | R10 | Y | Y | Y | >120* | >120 | 55.0 | Meaningless | N/Avail. | N/Avail. | ≧NC |
| S2 | R11 | Y | Y | Y | >120* | >120 | 80.0 | Meaningless | N/Avail. | N/Avail. | ≧NC |
| S2 | R12 | Y | Y | Y | >120* | >120 | 80.0 | Meaningless | N/Avail. | N/Avail. | ≧NC |
| S2 | R13 | Y | Y | Y | >120 | >120 | 55.0 | Meaningless | N/Avail. | N/Avail. | ≧NC |

Segment 1 Variation of starting membrane properties
Segment 2 Vaiation of line speed and dryer temperature

TABLE 5A

MODIFICATION DATA FOR Hydrophilic PVDF Western Blotting Membrane

| Run Segment | Roll No. | Monomer Mix Lot# | Starting Membrane Lot Data | Good Footage | Heat Treat Temperature or Mod Line Dryer Temperature | Membrane Casting Dryer Temperature |
|---|---|---|---|---|---|---|
| RUN T—POROSITY/THICKNESS, VMF4 DRYER TEMP, LINESPEED |||||||
| 1 | NA | 010908M1 | DRUM | 0 | NA | NA |
| 1 | NA | 010908M1-MM1 | Tank | 0 | NA | NA |
| 1 | NA | 010908M1-MM2 | Tank Diluted | 0 | NA | NA |
| 1 | R01 | 010908M1 | IPVH 050107 T101B | 155 | 200 | |
| 1 | R02 | 010908M1 | IPFL 071007 T203 | 90 | 200 | 300 |
| 2 | R03 | 010908M1 | IPX 120307 T109 | 90 | 200 | 300 |
| 2 | R04 | 010908M1 | IPX 120307 T109 | 90 | 200 | 300 |
| 2 | R05 | 010908M1 | IPX 120307 T109 | 90 | Transition | 300 |
| 2 | R06 | 010908M1 | IPX 120307 T109 | 90 | 220 | 300 |

TABLE 5A-continued

MODIFICATION DATA FOR Hydrophilic PVDF Western Blotting Membrane

| Run Segment | Roll No. | Monomer Mix Lot# | Starting Membrane Lot Data | Good Footage | Heat Treat Temperature or Mod Line Dryer Temperature | Membrane Casting Dryer Temperature |
|---|---|---|---|---|---|---|
| 2 | R07 | 010908M1 | IPX 120307 T109 | 90 | 215 | 300 |
| 2 | R08 | 010908M1 | IPX 120307 T109 | 90 | 215 | 300 |
| 2 | R09 | 010908M1 | IPX 120307 T109 | 90 | Transition | 300 |
| 2 | R10 | 010908M1 | IPX 120307 T109 | 90 | 220 | 300 |
| 3 | R11 | 010908M1 | IPX 091407 T101 | 10 | 205.4 | 300 |
| 3 | R12 | 010908M1 | IPX 071007 T213 | 90 | 205.5 | 300 |
| 3 | R13 | 010908M1 | IPX 120307 T104 | 90 | 205.8 | 300 |
| 3 | R14 | 010908M1 | IPX 070907 T105 | 90 | 206.1 | 300 |
| 3 | R15 | 010908M1 | IPX 070907 R102 | 90 | 205 | 300 |
| 3 | R16 | 010908M1 | IPX 070907 R106 | 90 | 205 | 300 |
| 3 | R17 | 010908M1 | IPX 120307 R110 | 90 | 205 | 300 |
| 3 | NA | 010908M1 | NA | 0 | 205 | |

Segment 1 Diagnostic

Segment 2 Dryer Temperature & Linespeed Variation

Segment 3 Porosity and Thickness Variation—Starting Membrane

TABLE 5B

MODIFICATION DATA FOR Hydrophilic PVDF Western Blotting Membrane

| Run Segment | Roll No. | Starting Membrane Properties | | | | Monomer Mix Sample ID | Monomer Mix Samples and Component Concentrations | | | | Totalized Footage By Roll |
|---|---|---|---|---|---|---|---|---|---|---|---|
| | | Thick (um) | Porosity (%) | Bbl Pt (psi) | Flow Time (seconds) | | Actual AC Wt % (HPLC) | Actual MBAM Wt % (HPLC) | Actual I-2959 Wt % (HPLC) | Actual Total Solids Wt % (HPLC) | |
| RUN T—POROSITY/THICKNESS, VMF4 DRYER TEMP, LINESPEED | | | | | | | | | | | |
| 1 | NA | NA | NA | NA | NA | DRUM | 0.76 | 0.60 | 0.15 | 1.51 | 0 |
| 1 | NA | NA | NA | NA | NA | MM1 | 0.75 | 0.58 | 0.15 | 1.48 | 0 |
| 1 | NA | NA | NA | NA | NA | MM2 Start | 0.51 | 0.40 | 0.10 | 1.00 | 0 |
| 1 | R01 | 109-125 | Not Available | Not Available | Not Available | Not Taken | NA | NA | NA | NA | 375 |
| 1 | R02 | 112 | 72.8 | 9.6 | 61.0 | Not Taken | NA | NA | NA | NA | 675 |
| 2 | R03 | 120 | 71.0 | 9.5 | 63.0 | MM3 | 0.50 | 0.39 | 0.10 | 0.99 | 775 |
| 2 | R04 | 120 | 71.0 | 9.5 | 63.0 | Not Taken | NA | NA | NA | NA | 875 |
| 2 | R05 | 120 | 71.0 | 9.5 | 63.0 | Not Taken | NA | NA | NA | NA | 975 |
| 2 | R06 | 120 | 71.0 | 9.5 | 63.0 | Not Taken | NA | NA | NA | NA | 1075 |
| 2 | R07 | 120 | 71.0 | 9.5 | 63.0 | Not Taken | NA | NA | NA | NA | 1175 |
| 2 | R08 | 120 | 71.0 | 9.5 | 63.0 | Not Taken | NA | NA | NA | NA | 1275 |
| 2 | R09 | 120 | 71.0 | 9.5 | 63.0 | Not Taken | NA | NA | NA | NA | 1375 |
| 2 | R10 | 120 | 71.0 | 9.5 | 63.0 | Not Taken | NA | NA | NA | NA | 1675 |
| 3 | R11 | 118 | 66.7 | 8.3 | 46.7 | MM4 | 0.48 | 0.38 | 0.09 | 0.96 | 1775 |
| 3 | R12 | 116 | 72.3 | 9.0 | 56.0 | Not Taken | NA | NA | NA | NA | 1875 |
| 3 | R13 | 119 | 72.4 | 9.7 | 66.0 | Not Taken | NA | NA | NA | NA | 1975 |
| 3 | R14 | 130 | 74.7 | 10.7 | 74.0 | Not Taken | NA | NA | NA | NA | 2075 |
| 3 | R15 | 134 | 73.4 | 9.9 | 65.0 | Not Taken | NA | NA | NA | NA | 2175 |
| 3 | R16 | 114 | 72.4 | 9.7 | 67.0 | Not Taken | NA | NA | NA | NA | 2275 |
| 3 | R17 | 113 | 70.2 | 9.4 | 61.0 | Not Taken | NA | NA | NA | NA | 2375 |
| 3 | NA | NA | NA | NA | NA | MM5 | 0.47 | 0.37 | 0.09 | 0.94 | 2675 |

Segment 1 Diagnostic

Segment 2 Dryer Temperature & Linespeed Variation

Segment 3 Porosity and Thickness Variation—Starting Membrane

TABLE 5C

MODIFICATION DATA FOR Hydrophilic PVDF Western Blotting Membrane

| Run Segment | Roll No. | Nip Aisle Press psi | Nip Wall Press psi | Line Speed ft/min | N₂ Flow Top/Bottom (SCFM) | UV P1 Inch HWC | UV P3 Inch HWC | UV P2 Inch HWC | Starting O₂ Level (ppm) |
|---|---|---|---|---|---|---|---|---|---|
| | | | | | RUN T—POROSITY/THICKNESS, VMF4 DRYER TEMP, LINESPEED | | | | |
| 1 | NA | 20 | 20 | NA | NA | NA | NA | NA | NA |
| 1 | NA | 20 | 20 | NA | NA | NA | NA | NA | NA |
| 1 | NA | 20 | 20 | NA | NA | NA | NA | NA | NA |
| 1 | R01 | 20 | 20 | 18 | 10/9.5 | 0.9 | 1.4 | 1.0 | 52.0 |
| 1 | R02 | 20 | 20 | 20 | 10/9.5 | 0.9 | 1.4 | 1.0 | 77.0 |
| 2 | R03 | 20 | 20 | 22-20 | 10/9.5 | 0.9 | 1.4 | 1.0 | 78.0 |
| 2 | R04 | 20 | 20 | 18 | 10/9.5 | 0.9 | 1.4 | 1.0 | 44.0 |
| 2 | R05 | 20 | 20 | 18 | 10/9.5 | 0.9 | 1.4 | 1.0 | 32.0 |
| 2 | R06 | 20 | 20 | 18 | 10/9.5 | 0.9 | 1.4 | 1.0 | 32.0 |
| 2 | R07 | 20 | 20 | 22-20 | 10/9.5 | 0.9 | 1.4 | 1.0 | 30.0 |
| 2 | R08 | 20 | 20 | 18 | 10/9.5 | 0.9 | 1.4 | 1.0 | 26.0 |
| 2 | R09 | 20 | 20 | 18-20 | 10/9.5 | 0.9 | 1.4 | 1.0 | 20.0 |
| 2 | R10 | 20 | 20 | 20 | 10/9.5 | 0.9 | 1.4 | 1.0 | 22.0 |
| 3 | R11 | 20 | 20 | 20 | 10/9.5 | 0.9 | 1.4 | 1.0 | 38.0 |
| 3 | R12 | 20 | 20 | 20 | 10/9.5 | 0.9 | 1.4 | 1.0 | 34.0 |
| 3 | R13 | 20 | 20 | 20 | 10/9.5 | 0.9 | 1.4 | 1.0 | 41.0 |
| 3 | R14 | 20 | 20 | 20 | 10/9.5 | 0.9 | 1.4 | 1.0 | 21.0 |
| 3 | R15 | 20 | 20 | 20 | 10/9.5 | 0.9 | 1.4 | 1.0 | 21.0 |
| 3 | R16 | 20 | 20 | 20 | 10/9.5 | 0.9 | 1.4 | 1.0 | 21.0 |
| 3 | R17 | 20 | 20 | 20 | 10/9.5 | 0.9 | 1.4 | 1.0 | 21.0 |
| 3 | NA | NA | NA | NA | NA | NA | NA | NA | NA |

Segment 1 Diagnostic
Segment 2 Dryer Temperature & Linespeed Variation
Segment 3 Porosity and Thickness Variation—Starting Membrane

TABLE 5D

MODIFICATION DATA FOR Hydrophilic PVDF Western Blotting Membrane

| Run Segment | Roll No. | Water Wet Speed OK? | Water Wet Uniform X-web? | Water Wet Through OK? | Speckle Level OK? | Opacity/ Translucence OK? | Salt Wet Time Seconds | Salt Wet Time Seconds | Salt Wet Time Seconds | Salt Wet Time Seconds | Fluores BKG RFU | QC Blotting Pass/Fail Control | Western Blotting Live Lysate |
|---|---|---|---|---|---|---|---|---|---|---|---|---|---|
| | | | | | | RUN T—POROSITY/THICKNESS, VMF4 DRYER TEMP, LINESPEED | | | | | | | |
| 1 | NA | NA | NA | NA | NA | NA | NA | NA | NA | NA | NA | NA | NA |
| 1 | NA | NA | NA | NA | NA | NA | NA | NA | NA | NA | NA | NA | NA |
| 1 | NA | NA | NA | NA | NA | NA | NA | NA | NA | NA | NA | NA | NA |
| 1 | R01 | Y | Y | Y | Y | Y | 2.4/5.6 | 3.4/6.2 | 3.1/6.2 | 3.0/6.0 | N/Avail. | N/Avail. | ≧NC |
| 1 | R02 | Y | Y | Y | Y | Y | 2.9/12.6 | 3.2/11.4 | 2.9/2.9 | 3.0/9.0 | N/Avail. | N/Avail. | ≧NC |
| 2 | R03 | Y | Y | Y | Y | Y | 1.1/24.1 | 1.4/10.8 | 1.1/4.1 | 1.2/13.0 | N/Avail. | N/Avail. | ≧NC |
| 2 | R04 | Y | Y | Y | Y | Y | 1.2/14.5 | 1.5/19.9 | 1.3/5.6 | 1.3/13.3 | N/Avail. | N/Avail. | ≧NC |
| 2 | R05 | Y | Y | Y | Y | Y | 1.3/10.5 | 1.5/15.4 | 1.3/4.2 | 1.4/10.0 | N/Avail. | N/Avail. | ≧NC |
| 2 | R06 | Y | Y | Y | Y | Y | 1.3/24.7 | 1.4/9.5 | 1.3/4.0 | 1.3/12.7 | N/Avail. | N/Avail. | ≧NC |
| 2 | R07 | Y | Y | Y | Y | Y | 2.5/60.0 | 2.3/25.4 | 2.5/5.4 | 2.4/30.0 | N/Avail. | N/Avail. | ≧NC |
| 2 | R08 | Y | Y | Y | Y | Y | 2.1/9.7 | 2.6/14.0 | 2.6/5.5 | 2.8/9.7 | N/Avail. | N/Avail. | ≧NC |
| 2 | R09 | Y | Y | Y | Y | Y | 2.8/13.1 | 3.5/22.6 | 2.5/5.9 | 2.9/13.9 | N/Avail. | N/Avail. | ≧NC |
| 2 | R10 | Y | Y | Y | Y | Y | 3.1/28.7 | 3.5/15.7 | 2.5/7.1 | 3.0/17.2 | N/Avail. | N/Avail. | ≧NC |
| 3 | R11 | Y | Y | Y | Y | Y | 24.1 | 6.5 | 4.2 | 11.6 | N/Avail. | N/Avail. | ≧NC |
| 3 | R12 | Y | Y | Y | Y | Y | 47.1 | 35.7 | 8.6 | 30.5 | N/Avail. | N/Avail. | ≧NC |
| 3 | R13 | Y | Y | Y | Y | Y | 67.9 | 70.7 | 34.5 | 57.7 | N/Avail. | N/Avail. | ≧NC |
| 3 | R14 | Y | Y | Y | N (HIGH) | N (White) | >180 | >180 | >180 | >180 | N/Avail. | N/Avail. | ≧NC |
| 3 | R15 | Y | Y | Y | N (HIGH) | N (White) | >180 | >180 | >180 | >180 | N/Avail. | N/Avail. | ≧NC |
| 3 | R16 | Y | Y | Y | N (HIGH) | Y | >180 | 57.3 | 16.4 | >180 | N/Avail. | N/Avail. | ≧NC |
| 3 | R17 | Y | Y | Y | Y | Y | 19.3 | 40.8 | 5.1 | 21.7 | N/Avail. | N/Avail. | ≧NC |
| 3 | NA | NA | NA | NA | NA | NA | NA | NA | NA | NA | NA | NA | NA |

Segment 1 Diagnostic
Segment 2 Dryer Temperature & Linespeed Variation
Segment 3 Porosity and Thickness Variation—Starting Membrane

EXAMPLE 3

The protocol used for Western blotting and chemiluminescent detection is as follows:

Protein samples are electrophoretically separated using Bis:Tris (4~12%) midi gradient gel (Invitrogen, WG1402BOX).

Samples are electro-blotted at 45V for 1 hr 15 min using BioRad tank transfer apparatus (Criterion Blotter #165-6024) onto a hydrophilic membrane prepared as in Example 1.

Blots are washed 2× (3 min each) in TBS-T (0.1% Tween)

Blots are blocked for 1 hr at RT in TBS-T with 3% NFM (non-fat milk, Carnation).

Blots are washed 2× (3 min each) in TBS-T (0.1% Tween)

Blots are incubated with primary antibody in TBS-T for 1 hr.

Blots are washed 3× (5 min each) in TBS-T (0.1% Tween)

Blots are incubated with secondary antibody in TBS-T for 1 hr

Blots are washed 4× (5 min each) in TBS-T (0.1% Tween)

Protein bands are visualized using ECL (Millipore Immobilon-HRP) and x-ray film.

Figure 1:
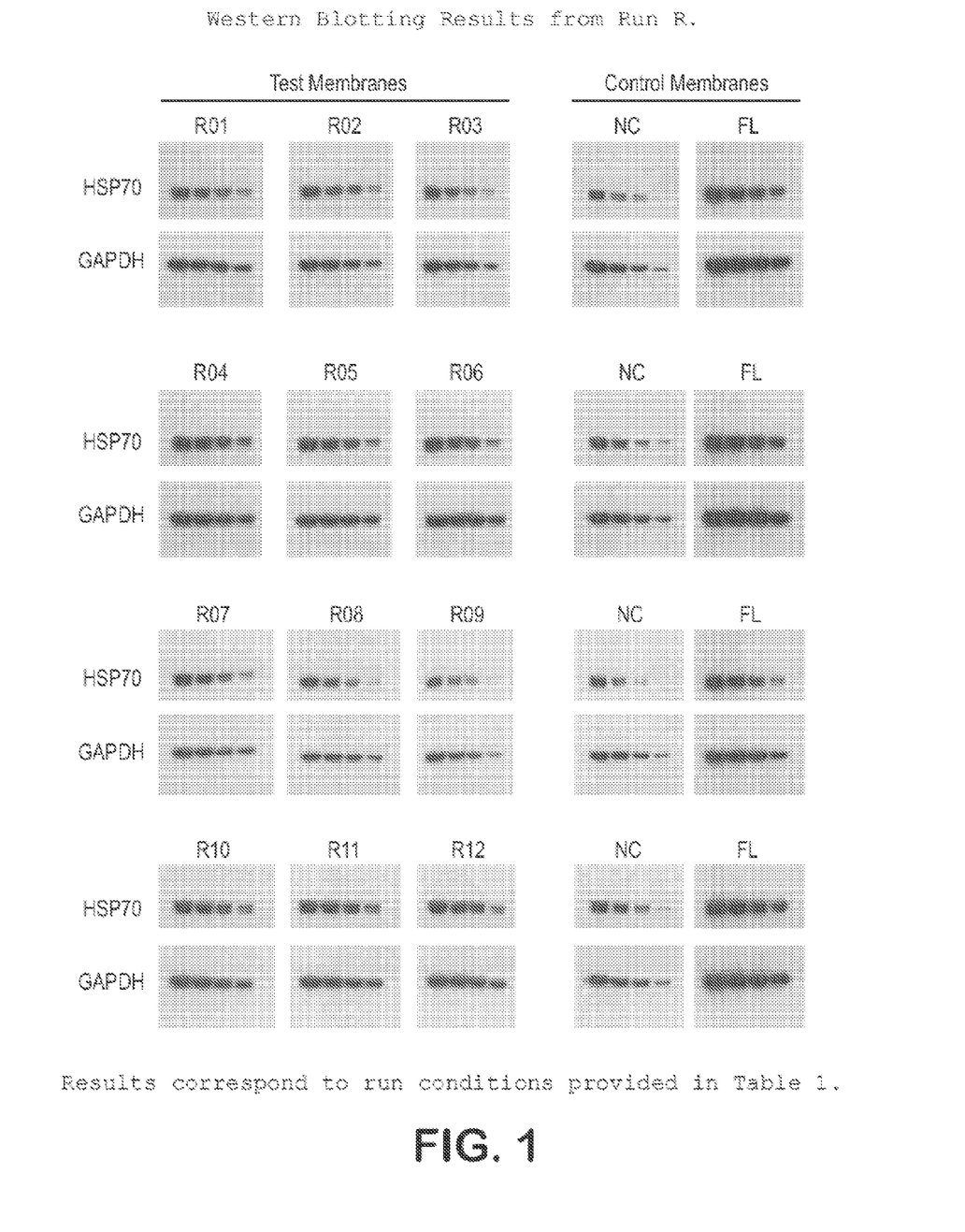
FIGS. 1-3 are diagrams of Western blot results using treated membranes in accordance with certain embodiments.
Figure 2:
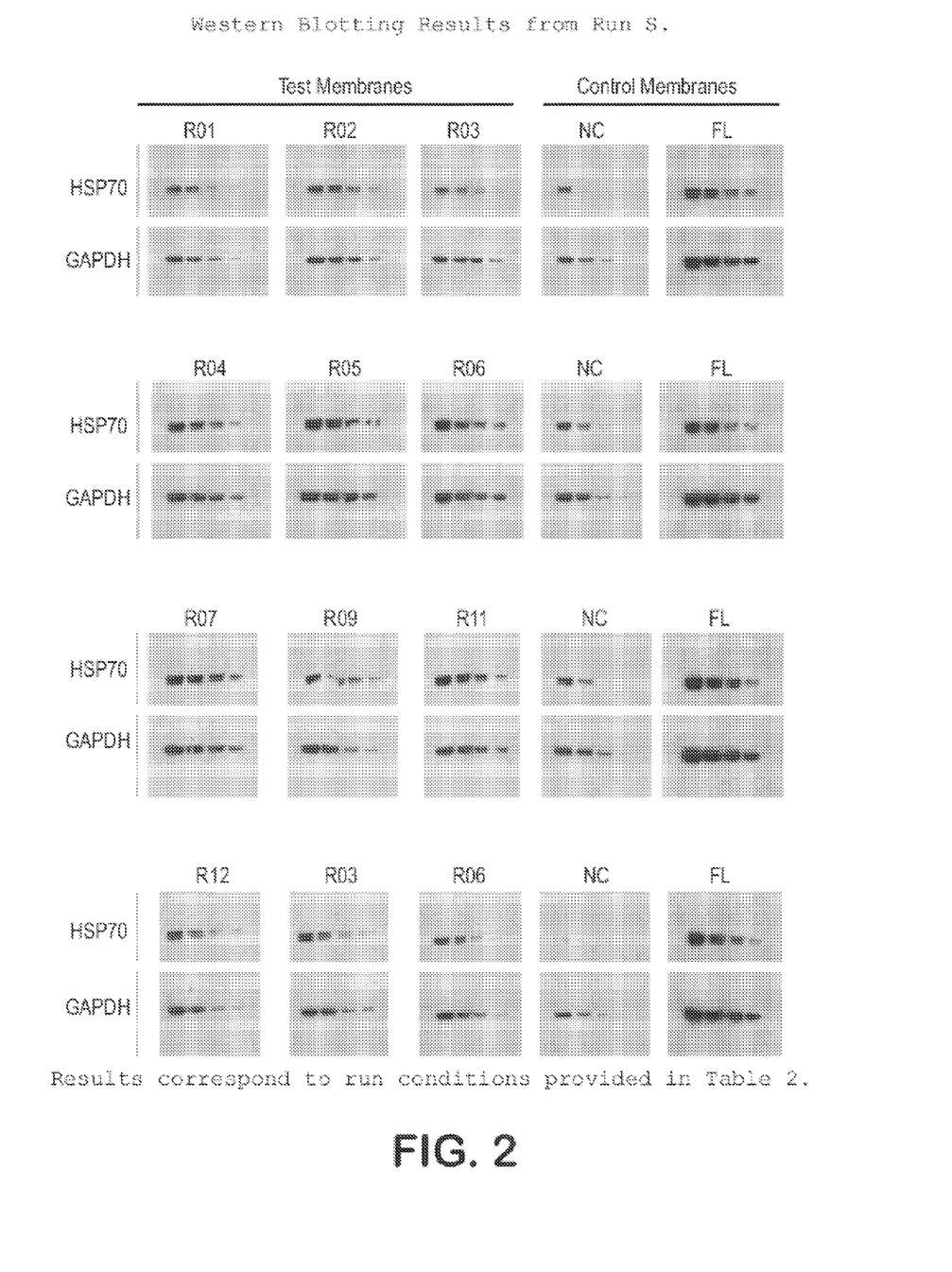
Figure 3:
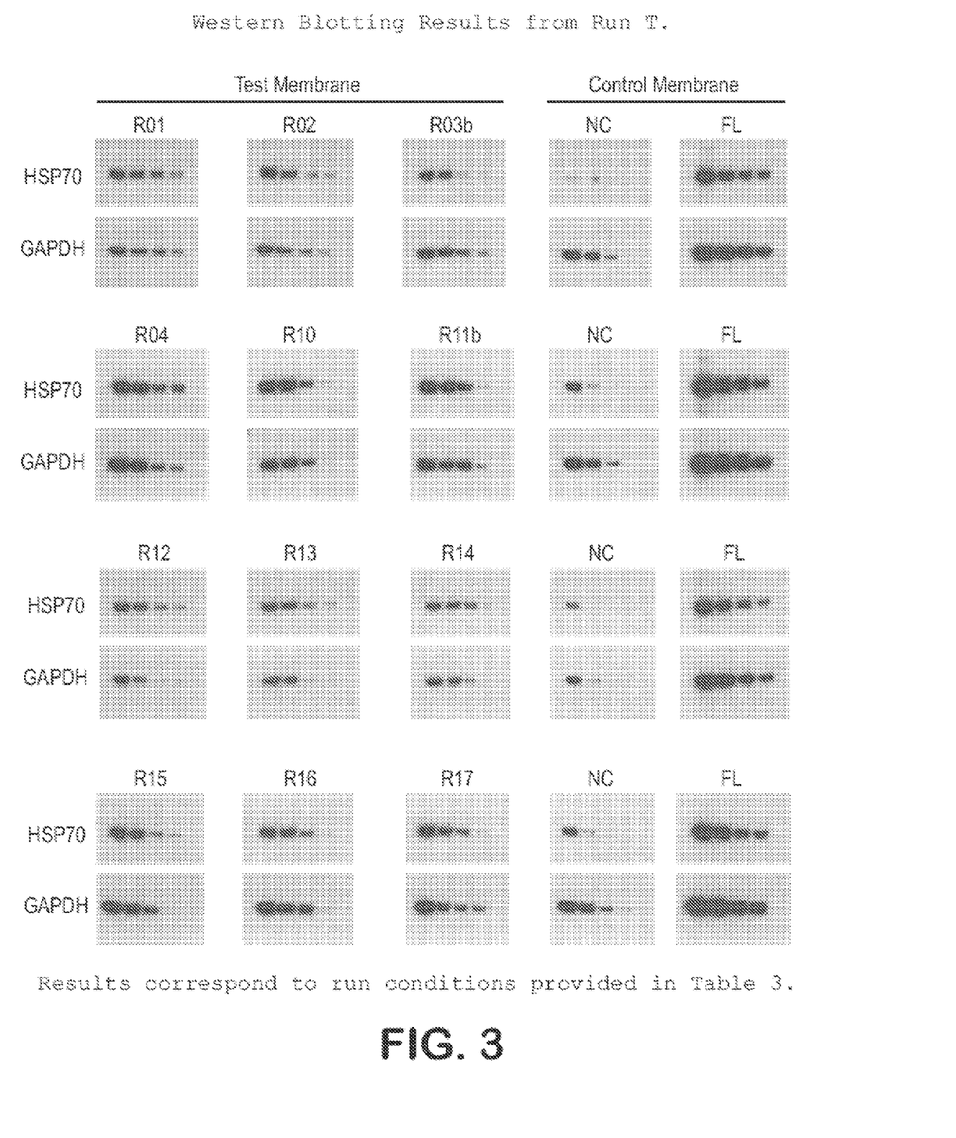

This protocol was used on the samples prepared in Example 2, and the blotting results are shown in FIGS. 1, 2, and 3.

Western blotting results from a typical development run demonstrate the performance differences between the hydrophilic PVDF blotting membrane of this invention, and the controls (FL—hydrophobic PVDF membrane, and NC—Whatman/S&S BA-85 membrane). Each horizontal strip in the figure contains 5 separate Western transfer blots; three blots on hydrophilic PVDF development samples, and one blot on each of the control membranes. Each strip of 5 Western blots is the result from one electrophoresis and transfer experiment (5 gels were run in each experiment). By design, each experiment embodies identical conditions with identical quantities of protein sample (applied in 4 lanes across each gel) before electrophoresis and transfer. The results shown are the transfer blots for the detection of 2 proteins (HSP70 and GAPDH) from a complex sample mixture (lysate), applied at decreasing sample solids (concentrations), from left-to-right and corresponding to: 5 ug, 2.5 ug, 1.25 ug, 0.67 ug.

Note that in each row (the result of a single electrophoresis and electro-blotting experiment, three hydrophilic blotting membranes of the invention are compared to two control blotting membranes. One control consists of nitrocellulose blotting membrane (NC) and the other control is a hydrophobic PVDF blotting membrane (FL). In the case of each single experiment, the FL membrane demonstrates the highest signal intensity for the 4 titers of analyte protein solution, and the NC membrane demonstrates the lowest signal intensity. It can be seen, when comparing the signal strengths between NC control blotting membranes and hydrophilic PVDF blotting membranes of the invention, that at the highest analyte sample titers (left hand side of each blot), that the NC and the hydrophilic PVDF membranes exhibit similar signal strengths. However, as one progresses to lower and lower analyte sample titers (progressing from left-to-right), the signal strength falls off more rapidly for the NC membrane. This demonstrates that the hydrophilic PVDF membrane allows sample detection at lower protein concentrations than NC membrane does.

What is claimed is:

1. A Western blot immunodetection assay for detecting target proteins in a protein sample, comprising:
    electrophoretically separating said target proteins from said protein sample;
    transferring the separated target proteins onto a porous polymeric substrate having its surface modified with a crosslinked polymeric coating comprising acrylamide and methylene-bis-acrylamide, said coating rendering said surface hydrophilic;
    blocking said substrate to prevent nonspecific binding of antibodies to said substrate surface;
    incubating said substrate with a primary antibody capable of binding to said target proteins;
    incubating said substrate with a labeled secondary antibody capable of complexing with an enzyme of said primary antibody to provide a measurable signal; and
    detecting said signal.

2. The Western blot immunodetection assay of claim 1, wherein the measurable signal is detected by visual, chemiluminescent or fluorescent detection.

3. The Western blot immunodetection assay of claim 1, wherein said porous polymeric substrate having its surface modified has a protein binding capacity as measured by an IgG binding test of about 250-325 $\mu g/cm^2$.

4. The Western blot immunodetection assay of claim 1, wherein the average total organic carbon level of said porous polymeric substrate is below 1.5 ug/$cm^2$, and wherein extractable monomer levels, as determined by HPLC, are below 0.02 ug/$cm^2$ for acrylamide, and below 0.15 ug/$cm^2$ for methylene-bis-acrylamide.

5. The Western blot immunodetection assay of claim 1, wherein said porous polymeric substrate has a background fluorescence value, and wherein said substrate modified with said polymeric coating exhibits a background fluorescence of about twice that of said substrate background fluorescence value under identical measurement conditions.

6. The Western blot immunodetection assay of claim 1, wherein said substrate comprises polyvinylidene fluoride.

7. The Western blot immunodetection assay of claim 1, wherein the ratio of acrylamide to methylene-bis-acrylamide is about 1:1 (mass/mass).

8. The Western blot immunodetection assay of claim 1, wherein the overall monomer concentration of the acrylamide:methylene-bis-acrylamide monomer reactant solution used to coat said surface is between 0.5% and 1.5% by mass.

* * * * *